United States Patent
Meister et al.

(10) Patent No.: US 11,426,581 B2
(45) Date of Patent: Aug. 30, 2022

(54) BILATERAL SYNCHRONIZED CHANNEL SELECTION FOR COCHLEAR IMPLANTS

(71) Applicant: MED-EL Elektromedizinische Geraete GmbH, Innsbruck (AT)

(72) Inventors: Dirk Meister, Innsbruck (AT); Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 708 days.

(21) Appl. No.: 16/339,065

(22) PCT Filed: Nov. 3, 2017

(86) PCT No.: PCT/US2017/059855
§ 371 (c)(1),
(2) Date: Apr. 3, 2019

(87) PCT Pub. No.: WO2018/085620
PCT Pub. Date: May 11, 2018

(65) Prior Publication Data
US 2020/0038659 A1    Feb. 6, 2020

Related U.S. Application Data

(60) Provisional application No. 62/417,396, filed on Nov. 4, 2016.

(51) Int. Cl.
*A61N 1/36* (2006.01)
*A61N 1/05* (2006.01)
*H04R 25/00* (2006.01)

(52) U.S. Cl.
CPC ....... *A61N 1/36038* (2017.08); *A61N 1/0541* (2013.01); *H04R 25/405* (2013.01);
(Continued)

(58) Field of Classification Search
CPC .............. A61N 1/36038; A61N 1/0541; A61N 1/36039; H04R 25/405; H04R 25/407; H04R 25/505; H04R 2225/67
See application file for complete search history.

(56) References Cited

U.S. PATENT DOCUMENTS 5,991,419 A * 11/1999 Brander ............... H04R 25/554
381/315
6,430,295 B1   8/2002 Händel et al.
(Continued)

FOREIGN PATENT DOCUMENTS

CN     1269902 A    10/2000
CN     1531371 A    9/2004
(Continued)

OTHER PUBLICATIONS

International Searching Authority/US, International Search Report and Written Opinion; Application No. PCT/US2017/059855, dated Jan. 8, 2018, 15 pages.
(Continued)

*Primary Examiner* — Catherine M Voorhees
*Assistant Examiner* — Roland Dinga
(74) *Attorney, Agent, or Firm* — Sunstein LLP

(57) ABSTRACT

A bilateral hearing implant system has a left side and a right side. Left and right side filter bank pre-processors preprocess left and right microphone signals to generate band pass signals for each side. A bilateral signal processing arrangement processes the band pass signals in a time sequence of stimulation frames. The signal processing module includes a bilateral channel selection module synchronously selects for each stimulation frame a set of stimulation channels for each side based on spectral content of the band pass signals. Left and right side signal processing submodules process for each stimulation frame a limited subset of each side band pass
(Continued)

signals corresponding to the selected stimulation channels to generate electrical stimulation signals.

21 Claims, 12 Drawing Sheets

(52) U.S. Cl.
CPC ......... *H04R 25/407* (2013.01); *H04R 25/505* (2013.01); *A61N 1/36039* (2017.08); *H04R 2225/67* (2013.01)

(56) References Cited

U.S. PATENT DOCUMENTS

| | | | |
|---|---|---|---|
| 7,310,558 B2 | 12/2007 | Van Hoesel | |
| 8,503,704 B2 | 8/2013 | Francart et al. | |
| 2004/0037442 A1* | 2/2004 | Nielsen | H04R 25/554 |
| | | | 381/315 |
| 2005/0107843 A1 | 5/2005 | McDermott et al. | |
| 2012/0128164 A1 | 5/2012 | Blamey | |
| 2013/0202119 A1 | 8/2013 | Thiede | |
| 2016/0016006 A1 | 1/2016 | Boyle | |
| 2016/0255443 A1 | 9/2016 | Backus | |
| 2018/0001089 A1* | 1/2018 | Meister | A61N 1/0541 |

FOREIGN PATENT DOCUMENTS

| | | |
|---|---|---|
| CN | 101582260 A | 11/2009 |
| CN | 103493512 A | 1/2014 |
| CN | 105007982 A | 10/2015 |
| CN | 105596119 A | 5/2016 |
| CN | 105920733 A | 9/2016 |
| WO | WO 2014/024032 A1 | 2/2014 |
| WO | WO 2016/089936 A1 | 6/2016 |

OTHER PUBLICATIONS

China National Intellectual Property Administration, Search Report, Application No. 201780067342.7, dated Oct. 21, 2020, English translation, 4 pages.

* cited by examiner

BILATERAL SYNCHRONIZED CHANNEL SELECTION FOR COCHLEAR IMPLANTS

This application claims priority from U.S. Provisional Patent Application 62/417,396, filed Nov. 4, 2016, which is incorporated herein by reference in its entirety.

FIELD OF THE INVENTION

The present invention relates to hearing implant systems, and more specifically to signal processing arrangements in bilateral cochlear implant systems.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus hearing implant systems include brainstem implants, middle brain implants, etc. each stimulating a specific auditory target in the auditory system.

FIG. 1 also shows some components of a typical cochlear implant system where an external microphone provides an audio signal input to an external implant processor 111 in which various signal processing schemes can be implemented. For example, it is well-known in the field that electrical stimulation at different locations within the cochlea 104 produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties). Examples of current signal processing approaches in the field of cochlear implants include continuous interleaved sampling (CIS) digital signal processing, channel specific sampling sequences (CSSS) digital signal processing (as described in U.S. Pat. No. 6,348,070, incorporated herein by reference), advanced combinational encoder (ACE) processing, spectral peak (SPEAK) digital signal processing, fine structure processing (FSP) and compressed analog (CA) signal processing.

Accordingly, the processed audio signal in the external implant processor 111 is converted into a digital data format for transmission by external transmitter coil 107 into an implant stimulator 108. Besides receiving the processed audio information, the implant stimulator 108 also performs additional signal processing such as error correction, pulse formation, etc., and produces stimulation signals (based on the extracted audio information) that are sent through an electrode lead 109 to an implanted electrode array 110. Typically, this electrode array 110 includes multiple electrode contacts 112 on its surface that provide selective stimulation of the cochlea 104.

In existing cochlear implant systems, the electrode contacts 112 are stimulated in a repeating time sequence of stimulation frames. If each stimulation frame uses all the electrode contacts 112, then the stimulation rate needs to be relatively low to accommodate the pulse lengths required to achieve a patient-specific sufficient loudness perception. Another drawback of stimulating all the electrode contacts 112 in a given stimulation frame is the interference between different channels due to overlapping electrical fields, residual charges at the neuron membranes, and higher order processes. There are several different approaches to reducing these negative effects which use a reduced subset of the electrode contacts 112. Channel selection then is performed frame-wise based on instantaneous signal properties such as band pass signal amplitude.

One widespread such scheme uses what is referred to as an n-of-m approach where only some number n electrode channels with the greatest amplitude are stimulated in a given stimulation frame. This approach is used, for instance, in the ACE and SPEAK strategies by Cochlear Corporation. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses.

In the CIS signal processing strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

Binaural stimulation has long been used in hearing aids, but it has only recently become common in hearing implants such as cochlear implants (CI). For cochlear implants, binaural stimulation requires a bilateral implant system with two implanted electrode arrays, one in each ear. The incoming left and right side acoustic signals are similar to those in hearing aids and may simply be the output signals of microphones located in the vicinity of the left and right ear, respectively.

FIG. 2 shows various functional blocks in a typical bilateral cochlear implant signal processing system. Independently on each side—left and right—an input sensing microphone 201 senses environmental sounds and coverts them into representative electrical signals that form audio inputs to the system. FIG. 3 shows a typical example of a short time period of an input audio signal from an input sensing microphone 201. The input audio signal is fed through multiple band pass filters (BPFs) 202 that decompose the input audio signal into multiple spectral band pass signals as shown, for example, in FIG. 4. As shown in FIG. 5, each band pass signal 501 is thought of as having a fine structure component 502 and an envelope component 503 (typically derived by Hilbert transformation). The filtered envelope signal 504 oscillates around the zero reference axis line with a frequency that is related to the fundamental frequency F0 of the band pass filter.

A non-linear dynamic processing module 203 dynamically adjusts the filter envelopes by adaptive processing such as with automatic gain control (AGC) and other dynamic signal processing adjustments. Envelope detectors 204 extract the slowly-varying band pass envelope components of the band pass signals, for example, by full-wave rectification and low pass filtering. Pulse timing module 205 modulates the envelope signals with the corresponding band pass carrier waveforms to produce stimulation pulse requests on which the mapping/pulse generation module 206 performs a non-linear (e.g., logarithmic) mapping to fit the patient's perceptual characteristics and produces electrode stimulation signals in the specific form of non-overlapping biphasic output pulses for each of the stimulation contacts (EL-1 to EL-n) of each electrode array implanted in each cochlea on the left and right sides reflecting the tonotopic neural response of the cochlea.

Bilateral cochlear implants provide the benefits of two-sided hearing which can allow a listener to localize sources of sound in the horizontal plane. That requires information from both ears such as interaural level differences (ILDs) and interaural time differences (ITDs). This is discussed further, for example, in Macpherson, E. A, and Middlebrooks, J. C., *Listener Weighting Of Cues For Lateral Angle: The Duplex Theory Of Sound Localization Revisited*, J. Acoust. Soc. Am. 111, 2219-3622, 2002, which is incorporated herein by reference. An ITD is a relative time shift between signals arriving at the left and right ear which is caused by different times for the signal to reach each ear when the source of sound is not within the median plane. An ILD is a similar difference in sound levels of signals entering the ears. Two-sided hearing also is known to make speech easier to understand in noise, and again the perception of ITD plays a pivotal role therein. This is explained more fully, for example, in Bronkhorst, A. W., and Plomp, R., *The Effect Of Head-Induced Interaural Time And Level Differences On Speech Intelligibility In Noise*, J. Acoust. Soc. Am. 83, 1508-1516, 1988, which is incorporated herein by reference.

SUMMARY OF THE INVENTION

Embodiments of the present invention are directed to systems and methods for bilateral hearing implant systems having a left side and a right side. Left side and right side sound environments are sensed with left side and right side sensing microphones to develop corresponding left and right microphone signals. The left and right microphone signals are preprocessed to generate band pass signals for each side, each band pass signal representing an associated band of audio frequencies. The band pass signals are processed in a time sequence of stimulation frames, and for each stimulation frame, the processing includes synchronously selecting a set of stimulation channels for each side based on spectral content of the band pass signals, and processing a limited subset of each side band pass signals corresponding to the selected stimulation channels to generate electrical stimulation signals for the left side and right side hearing implants for perception as sound by an implanted patient.

In further specific embodiments, the synchronously selecting uses a composite set of combined left and right band pass signals; for example, using one or more masking models. In addition or alternatively, the synchronously selecting may use a master-slave arrangement wherein one side of the bilateral hearing implant system is selected to be a master side configured for selecting the stimulation channels, and wherein the other side of the bilateral hearing implant system is a slave side configured for using the selected stimulation channels from the master side. In such embodiments, the master side may be the side on which the microphone signals are loudest and/or the side on which a dominant sound object is located. The synchronously selecting may choose a defined number of greatest amplitude band pass signals independently of side.

DETAILED DESCRIPTION OF SPECIFIC EMBODIMENTS

When applying a signal-specific channel selection in a bilateral implant system, the spectral distribution between the ears can differ; e.g., if there is a noise source present, that adds noise differently to both ears. In such circumstances, the channels that are selected for stimulation will be different on both sides of the implant system, and this in turn can provide different spectral cues of a desired source signal. This can be especially problematic when listening to musical instruments when different stimulation channels containing different harmonics are selected for stimulation on both sides of the implant system.

Until now, bilateral hearing implant systems have not synchronized of the spectral content of both sides of the system. Rather, selection of electrode stimulation channels on each side is performed independently of the other side. Embodiments of the present invention change that, and synchronize the channel selection on both sides of the bilateral implant system.

Figure 6:
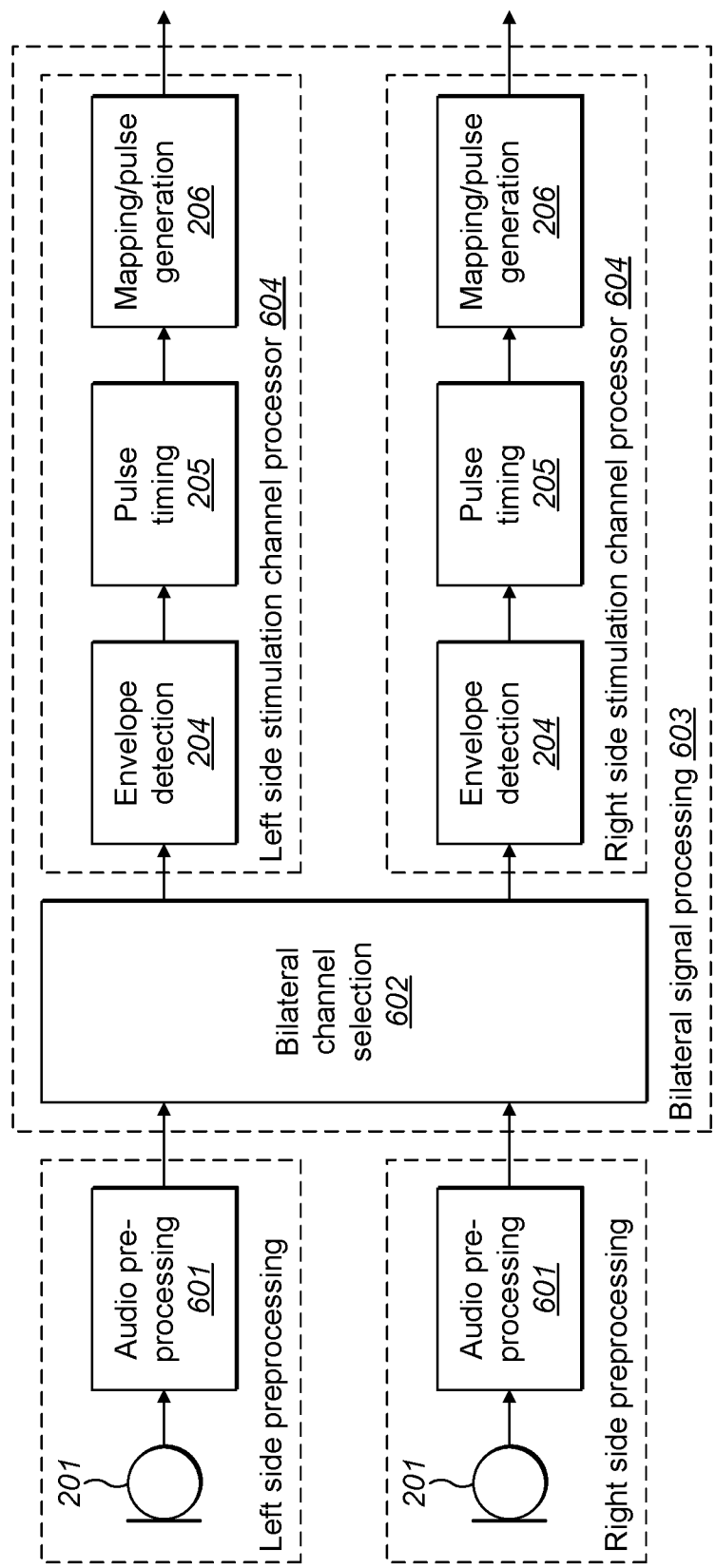
FIG. 6 shows various functional blocks in a bilateral cochlear implant signal processing arrangement with synchronized spectral content according to one specific embodiment of the present invention.
Figure 7:
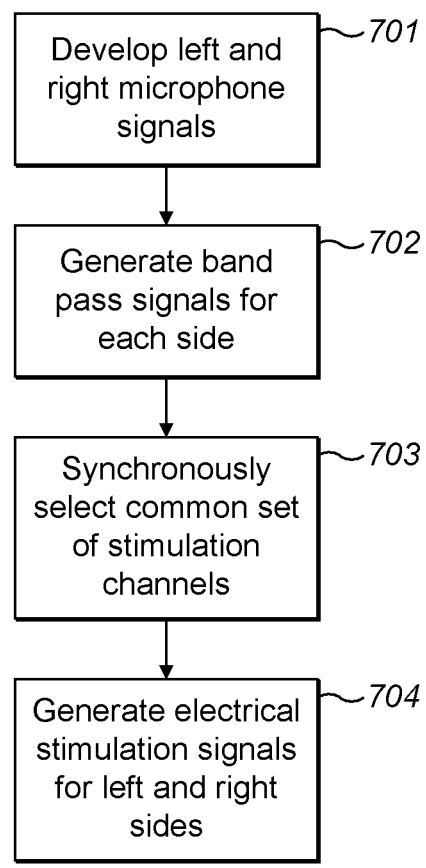
FIG. 7 shows various functional steps in processing stimulation signals with synchronized spectral content according to an embodiment of the present invention.

FIG. 6 shows various functional blocks in a signal processing arrangement for a bilateral hearing implant system and FIG. 7 is a flow chart showing various logical steps in synchronizing the spectral content of electrode stimulation signals on both sides of a bilateral hearing implant system. A pseudo code example of such a method can be set forth as:

```
Input Signal Preprocessing:
    LR_BandPassFilter (LR_input_sound, LR_band_pass_signals)
Channel Selection:
    ChannelSelect (LR_band_pass_signals, stimulation_channels)
Pulse Generation:
    PulseGenerate (LR_band_pass_signals, stimulation_channels,
                   out_pulses)
```

The details of such an arrangement are set forth in the following discussion.

In the arrangement shown in FIG. 6, the initial input sound signal is produced by left side and right side sensing microphones 201, which may be omnidirectional and/or directional, and which are configured for sensing left side and right side sound environments to develop corresponding left and right microphone signals, step 701.

Left side and right side audio preprocessors 601 are configured for preprocessing the left and right microphone signals to generate a plurality of band pass signals for each side, each band pass signal representing an associated band of audio frequencies, step 702, with a bank of multiple parallel band pass filters, each of which is associated with a specific band of audio frequencies; for example, using a filter bank with 12 digital Butterworth band pass filters of 6th order, Infinite Impulse Response (IIR) type, so that the input sound signal is filtered into multiple band pass signals where each signal corresponds to the band of frequencies for one of the band pass filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

Each output of the sufficiently narrow CIS band pass filters for a voiced speech input signal may roughly be regarded as a sinusoid at the center frequency of the band pass filter which is modulated by the envelope signal. This is also due to the quality factor (Q 3) of the filters. In case of a voiced speech segment, this envelope is approximately periodic, and the repetition rate is equal to the pitch frequency. Alternatively and without limitation, the left side and right side audio preprocessors 601 may be implemented based on use of a fast Fourier transform (FFT) or a short-time Fourier transform (STFT). Based on the tonotopic organization of the cochlea, each electrode contact in the scala tympani typically is associated with a specific band pass filter of the left side and right side audio preprocessors 601. The left side and right side audio preprocessors 601 also may perform other initial signal processing functions such as for example automatic gain control (AGC) and/or noise reduction and/or wind noise reduction and/or beamforming and other well-known signal enhancement functions.

Figure 1:
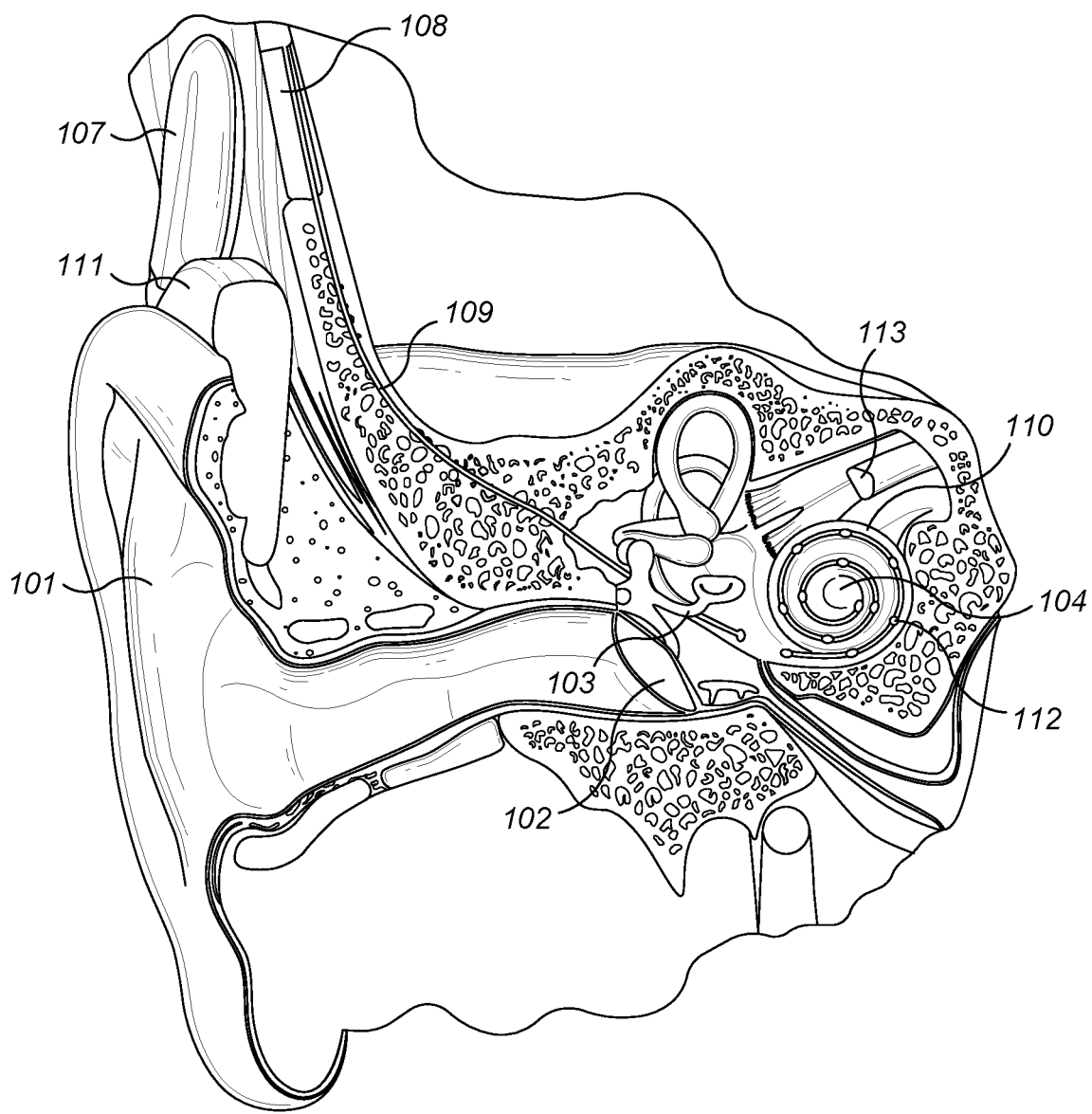
FIG. 1 shows a section view of a human ear with a typical hearing prosthesis system designed to deliver electrical stimulation to the inner ear.
Figure 2:
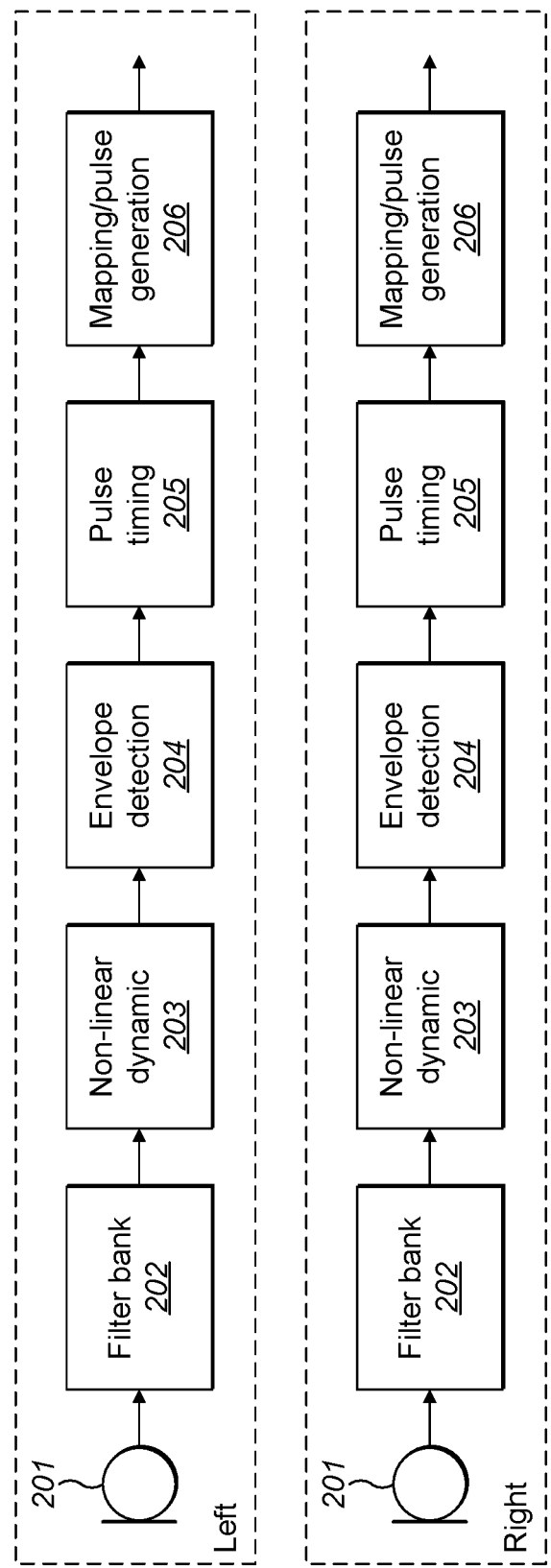
FIG. 2 shows various functional blocks in a typical bi-lateral cochlear implant signal processing arrangement.
Figure 3:
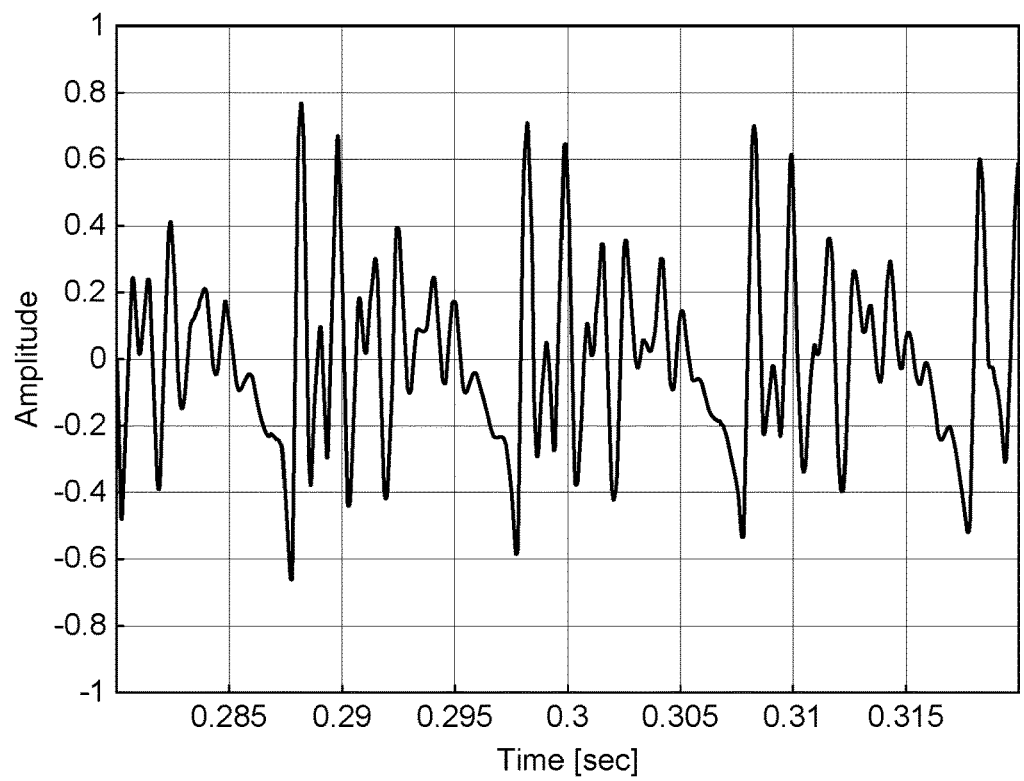
FIG. 3 shows an example of a short time period of an audio speech signal from a microphone.
Figure 4:
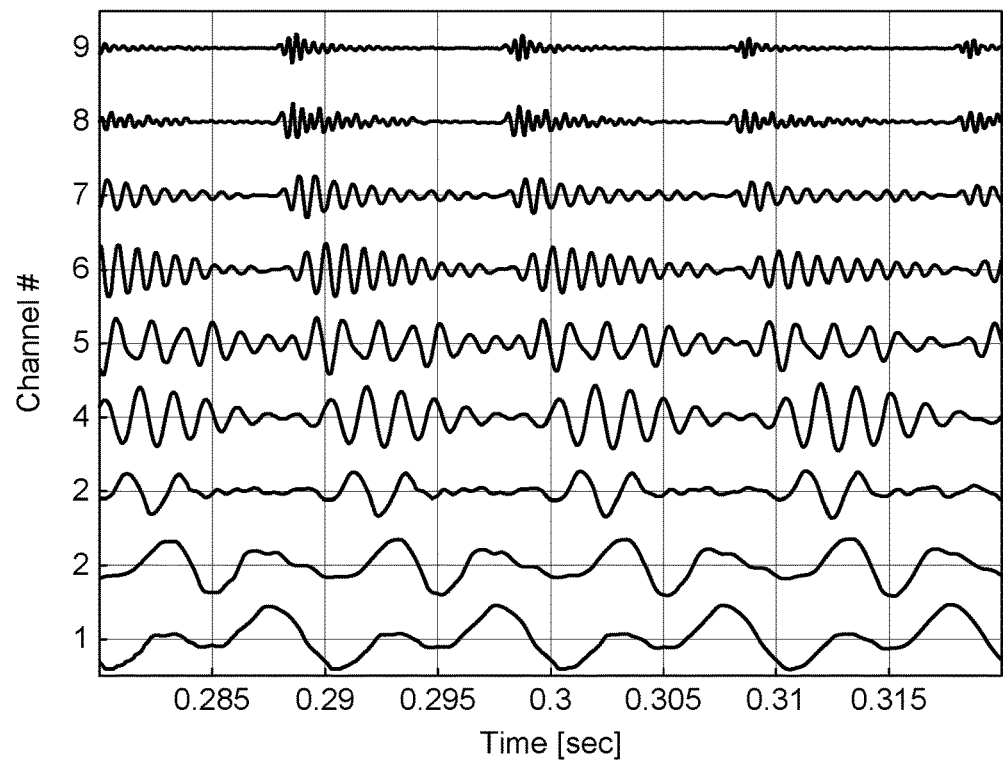
FIG. 4 shows an acoustic microphone signal decomposed by band-pass filtering by a bank of filters into a set of signals.
Figure 5:
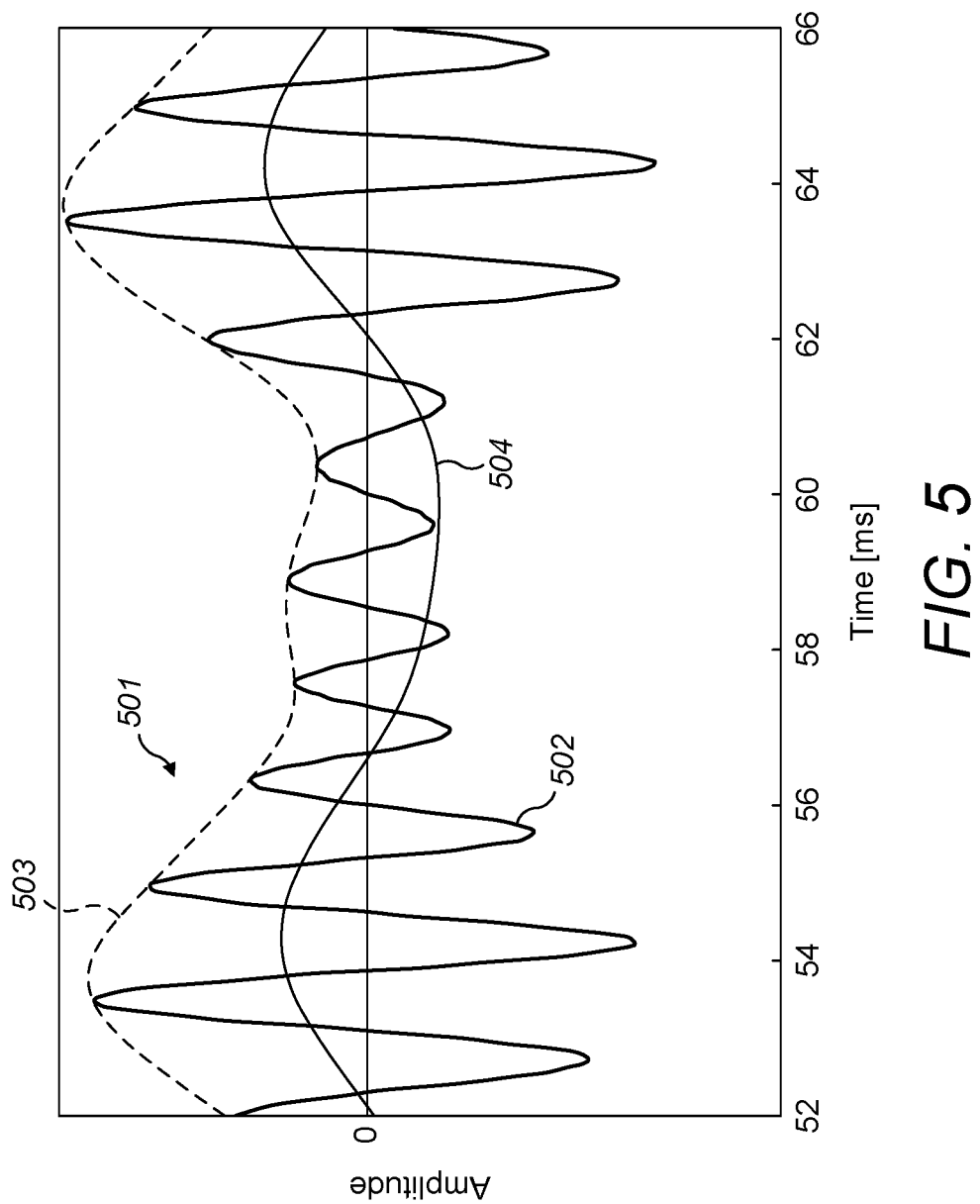
FIG. 5 shows a specific band pass signal and its various component parts.

The band pass signals (which can also be thought of as electrode channels) are output to a bilateral signal processing module 603 that processes the band pass signals in a time sequence of stimulation frames. The bilateral signal processing module 603 includes a bilateral channel selection module 602, configured for processing each stimulation frame to synchronously select a set of stimulation channels for each side based on spectral content of the band pass signals, step 703. Left and right side stimulation channel processors 604 then process for each stimulation frame a limited subset of each sides band pass signals that correspond to the selected stimulation channels to generate electrical stimulation signals for the left side and right side hearing implants for perception as sound by an implanted patient, step 704. For example, the left and right side stimulation channel processors 604 may use an arrangement as described above with respect to FIG. 2 with envelope detectors 204, pulse timing modules 205, and mapping/pulse generation modules 206.

More specifically, the bilateral channel selection module 602 may be configured to use a bilateral M×(1-of-2) scheme for selecting stimulation channels. In other words, the channel selection for each channel i and stimulation frame n and a pre-defined threshold value THR may be selected by the stimulation channel processors 604 according the following pseudo program code:

```
For each channel i
    if ENV_L (n, i) > ENV_R (n, i) •THR
        then ENV_R (n, i) = 0
    else if ENV_L (n, i) •THR < ENV_R (n, i)
        then ENV_L (n, i) = 0
end
```

In addition, a number N bilateral groups G of channels i may be formed comprising of left- and right-side channels, e.g. consisting of one channel on the left side and one channel on the right side with equivalent frequency settings. The former pseudo-code may then be applied for each group G and all channels within that group. In one embodiment, one or more groups may be omitted from the selection step 703 carried out by the stimulation channel processors 604. For example the group G formed by the low frequency channels may be omitted to avoid a degradation of lateral perception for the patient. In a further embodiment, the pre-defined threshold value THR may be different for each group and/or channel i and/or channel i within the group and/or left or right side. For example, the threshold value THR may be a function of the channel i, i.e. $THR(i)=f(i)$. More specifically a function of the bandwidth of the channel i: $THR(i)=f(BW_i)$.

In addition or alternatively, the bilateral channel selection module 602 may be configured to use an algorithm for synchronous channel selection that may be based on a fused signal of the left and right input signals, i.e., a composite set of combined left and right band pass signals. The bilateral channel selection module 602 may be specifically configured to synchronously select a pre-defined number of greatest amplitude band pass signals from the composite set, i.e. independently of side. In a first step the composite set if formed from the 1 . . . M channels of the left side channels and M+1 . . . 2M channels from the right side channels. Then the channel selection module 602 may pick out from the composite set those predetermined number N channels having the largest amplitude and irrespective of whether this is a left- or right side channel. As an example, Table 1 below shows one stimulation frame where each of eight stimulation channels appears once and is denoted with the displayed amplitudes:

TABLE 1

Left and right side channel amplitudes in an example stimulation frame

| Channel | 1 | 2 | 3 | 4 | 5 | 6 | 7 | 8 |
|---|---|---|---|---|---|---|---|---|
| L_Amplitude | 10 | 50 | 55 | 10 | 10 | 10 | 45 | 40 |
| R_Amplitude | 5 | 30 | 35 | 25 | 20 | 5 | 5 | 5 |

In such a case, selecting N=6 pre-determined channels would yield the following selection as shown in Table 2:

TABLE 2

Composite n-of-m selection.

| Channel | 1 | 2 | 3 | 4 | 5 | 6 | 7 | 8 |
|---|---|---|---|---|---|---|---|---|
| nL |  | x | x |  |  |  | x | x |
| nR |  | x | x |  |  |  |  |  |

In addition or alternatively, the bilateral channel selection module 602 may be configured to use a master-slave arrangement for synchronously selecting stimulation channels. One side of the bilateral hearing implant system can be selected to be a master side configured for selecting the stimulation channels, and the other side of the bilateral hearing implant system can be a slave side configured for using the selected stimulation channels from the master side. For example, the master side may be the side on which the microphone signals are loudest and/or the side on which a dominant sound object is located. As an example, Table 3 below shows one stimulation frame where each of eight stimulation channels appears once and is denoted with the displayed amplitudes:

TABLE 3

Left and right side channel amplitudes in an example stimulation frame

| Channel | 1 | 2 | 3 | 4 | 5 | 6 | 7 | 8 |
|---|---|---|---|---|---|---|---|---|
| L_Amplitude | 10 | 50 | 55 | 10 | 10 | 10 | 45 | 40 |
| R_Amplitude | 5 | 30 | 35 | 25 | 20 | 5 | 5 | 5 |

In such a case, a typical, non-bilateral synchronized 4-of-8 selection would yield the following selection as shown in Table 4:

TABLE 4

Independent n-of-m selection.

| Channel | 1 | 2 | 3 | 4 | 5 | 6 | 7 | 8 |
|---|---|---|---|---|---|---|---|---|
| nL |  | x | x |  |  |  | x | x |
| nR |  | x | x | x | x |  |  |  |

In this example according an embodiment of the invention the left channel is selected to be the master and the right channel to be slave. The criterion used in this example are the envelope amplitudes, which reflect signal energy or loudness. Accordingly, where bilateral stimulation channels are synchronously selected with the higher amplitude left side selected as the master side, the synchronously selected stimulation channels (on both sides) would be as shown in Table 5:

Table 5

| A master selection with the higher amplitude left side as a master. | | | | | | | | |
|---|---|---|---|---|---|---|---|---|
| Channel | 1 | 2 | 3 | 4 | 5 | 6 | 7 | 8 |
| nL |  | x | x |  |  |  | x | x |
| nR |  | x | x |  |  |  | x | x |

Alternatively to a strict master-slave relationship, the bilateral channel selection module 602 may be configured to first perform an n-of-m selection separately on both sides yielding nL for the left side and nR for the right side, then the bilateral channel selection module 602 can calculate the common numbers of selected channels nLR from the two side-specific numbers nL and nR, e.g. as a superposition as nLR=nL OR nR. An "OR" selection would yield a 6-of-8 selection:

TABLE 6

| Superposition of left and right n-of-m. | | | | | | | | |
|---|---|---|---|---|---|---|---|---|
| Channel | 1 | 2 | 3 | 4 | 5 | 6 | 7 | 8 |
| nL |  | x | x | x | x |  | x | x |
| nR |  | x | x | x | x |  | x | x |

In a further implementation, the bilateral channel selection module 602 may be configured to pool all channels mL and mR and select the n highest as shown in Table 7:

TABLE 7

| Overall winners take it all, 6-of-(2xM). | | | | | | | | |
|---|---|---|---|---|---|---|---|---|
| Channel | 1 | 2 | 3 | 4 | 5 | 6 | 7 | 8 |
| nL |  | x | x |  |  |  | x | x |
| nR |  | x | x |  |  |  |  |  |

This configuration would enhance large ILDs according to a "winner takes it all" principle. A special case of n-of-m is 1-of-2, especially if the larger of bilateral channel pairs is selected. Bilateral pairs can be compiled of identical band pass channels ([ch1 L/ch1 R], [ch2 L/ch2 R]) as depicted in Table 8 or alternating channels (e.g., ([ch1 L/ch2 R], [ch2 L/ch1 R])):

TABLE 8

| Winner takes it all, Mx(1-of-2). | | | | | | | | |
|---|---|---|---|---|---|---|---|---|
| Channel | 1 | 2 | 3 | 4 | 5 | 6 | 7 | 8 |
| nL | x | x | x |  |  | x | x | x |
| nR |  |  |  | x | x |  |  |  |

Figure 8A:
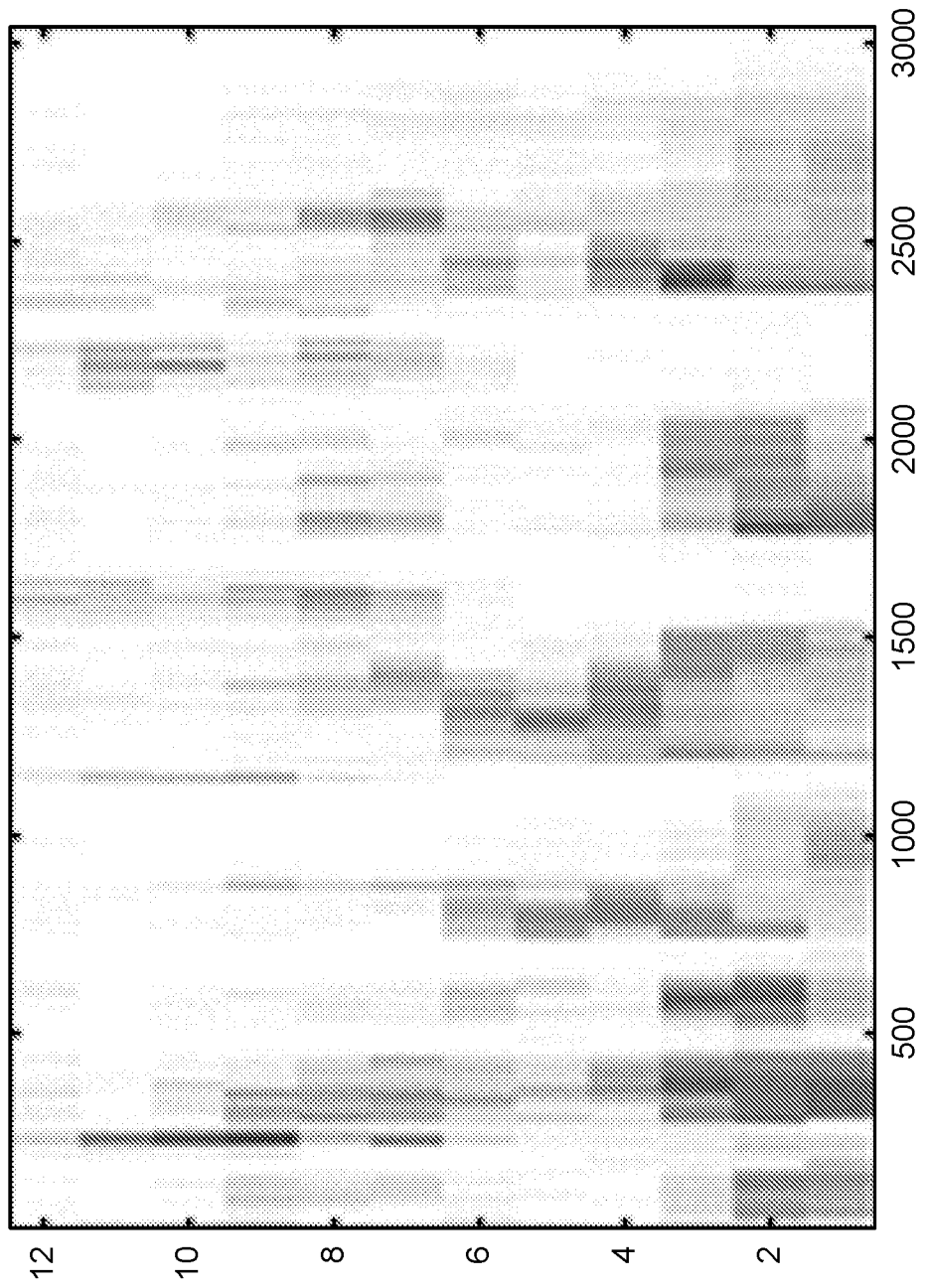
FIGS. 8A-8B show examples of left and right band pass envelopes for speech in a quiet environment.
Figure 8B:
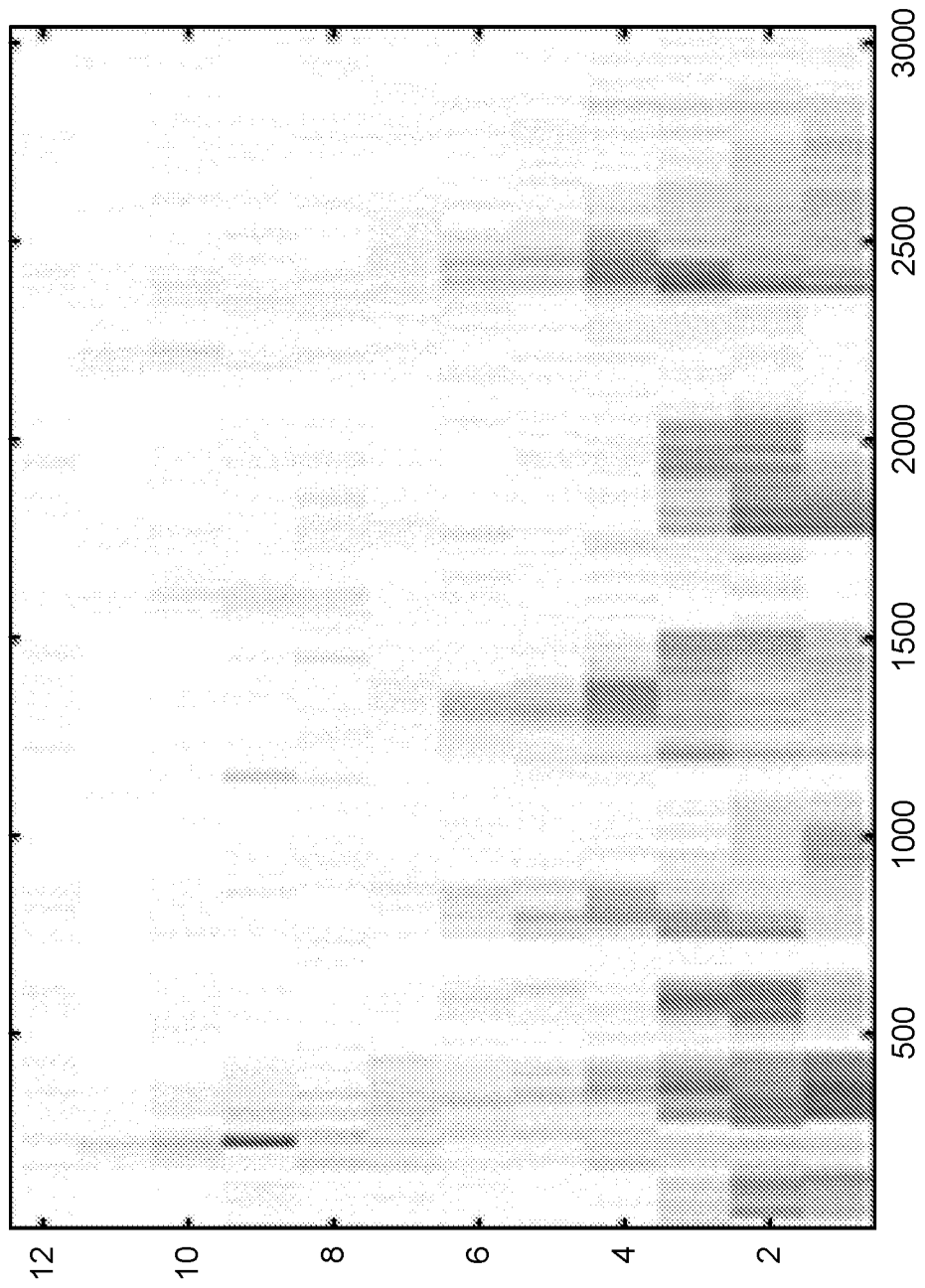
Figure 9A:
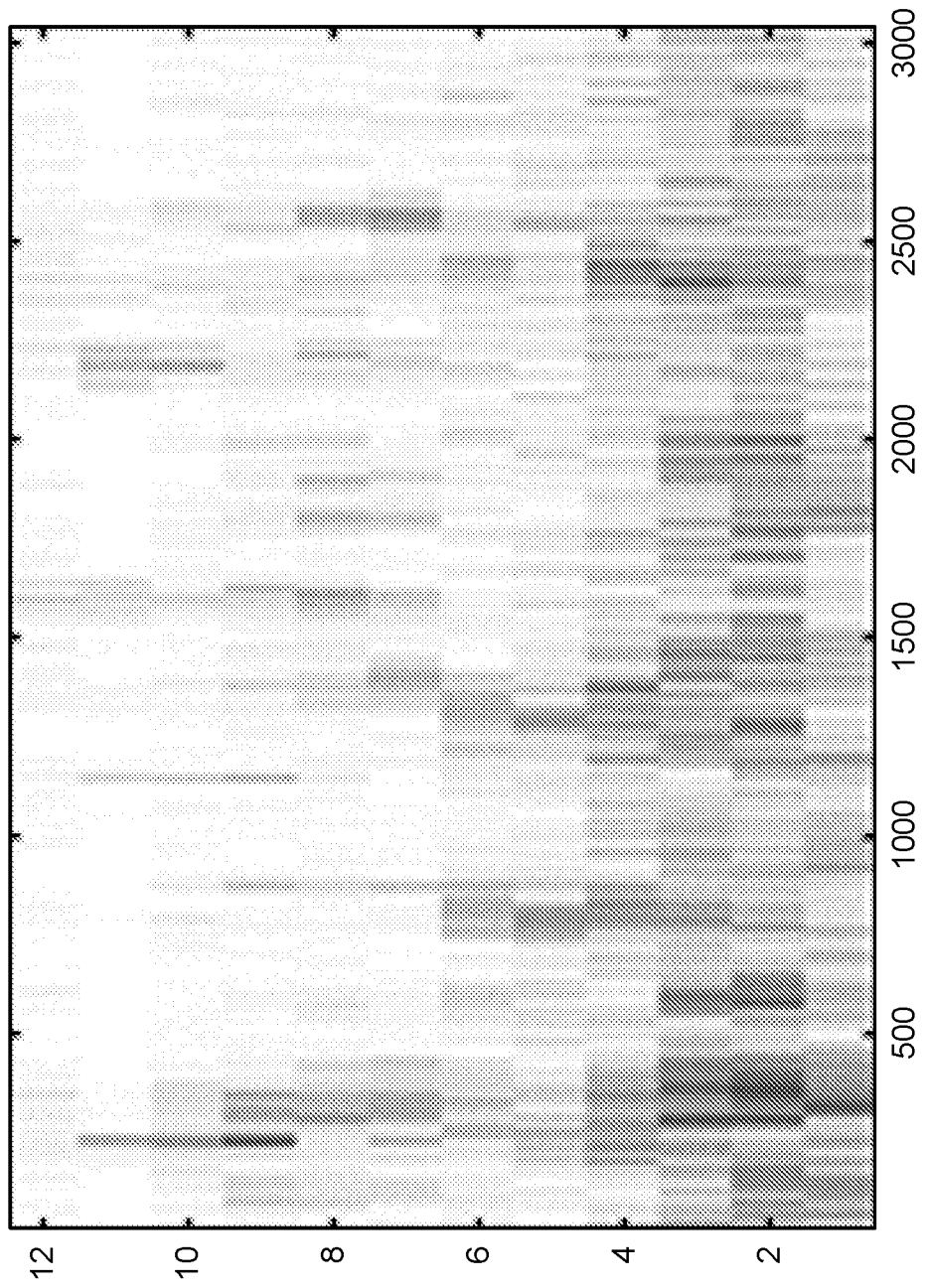
FIGS. 9A-9B show examples of original left and right band pass envelopes for speech in a noisy environment.
Figure 9B:
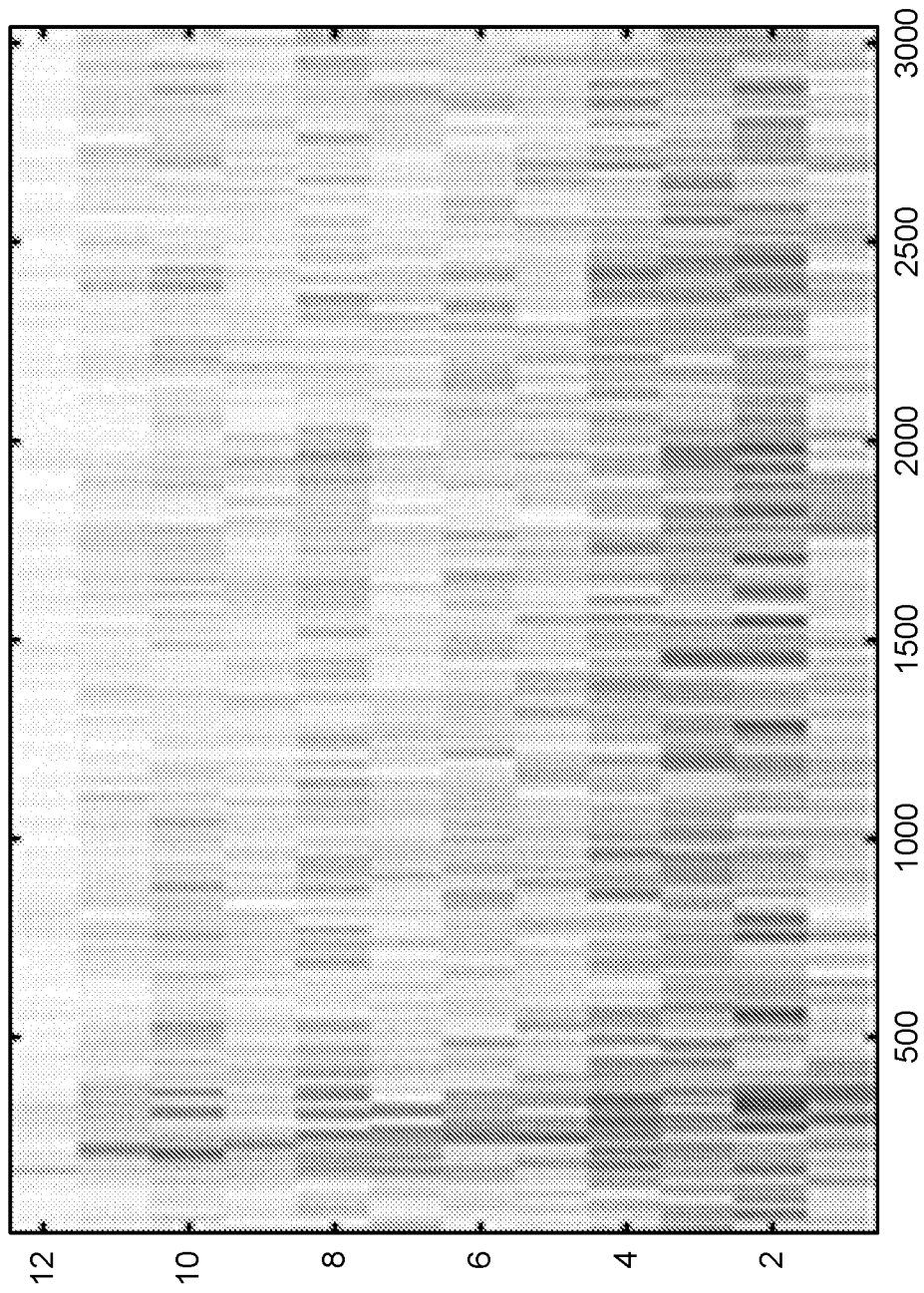
Figure 10A:
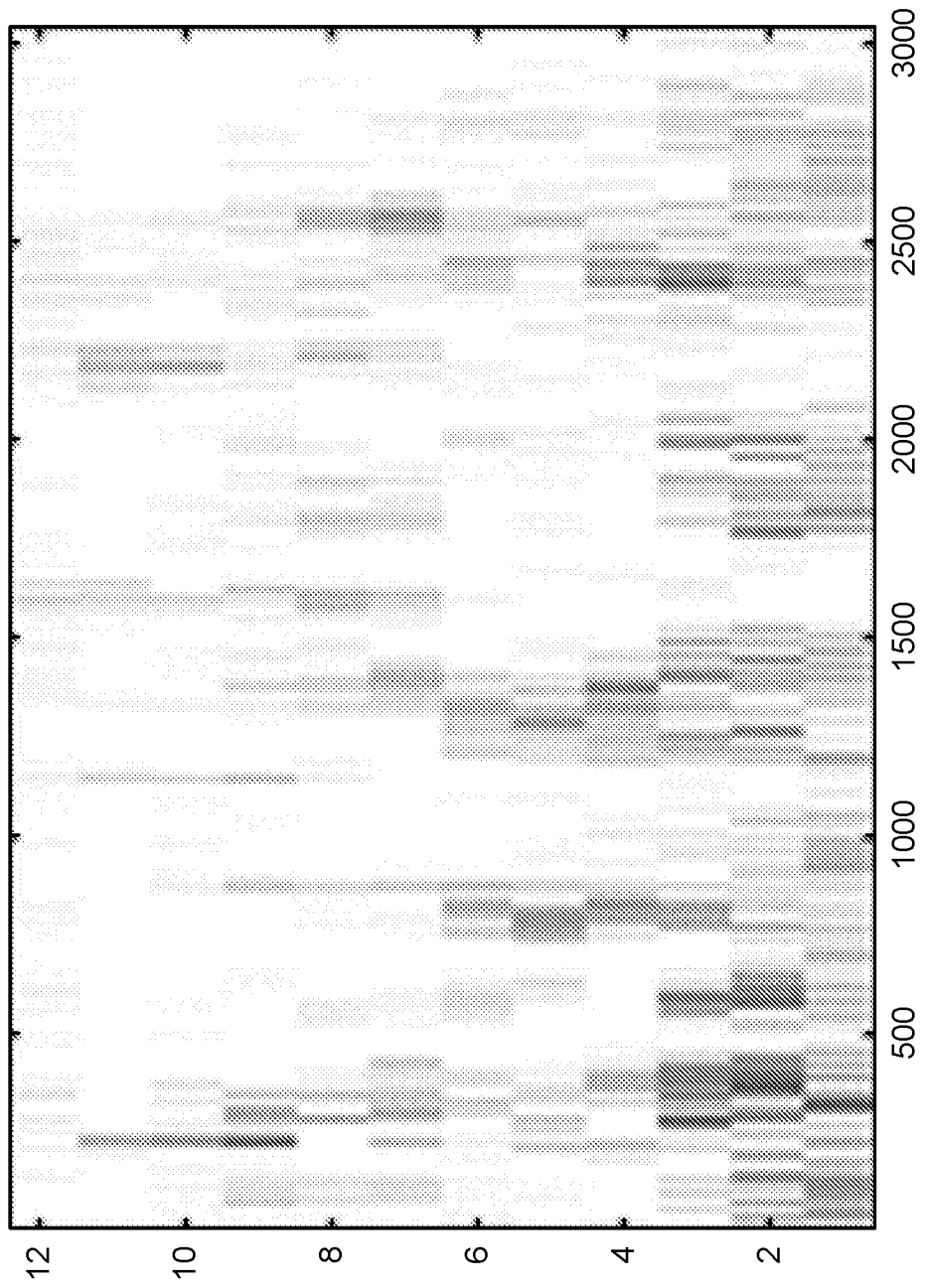
FIGS. 10A-10B show examples of bilaterally selected left and right band pass envelopes according to an embodiment of the present invention.
Figure 10B:
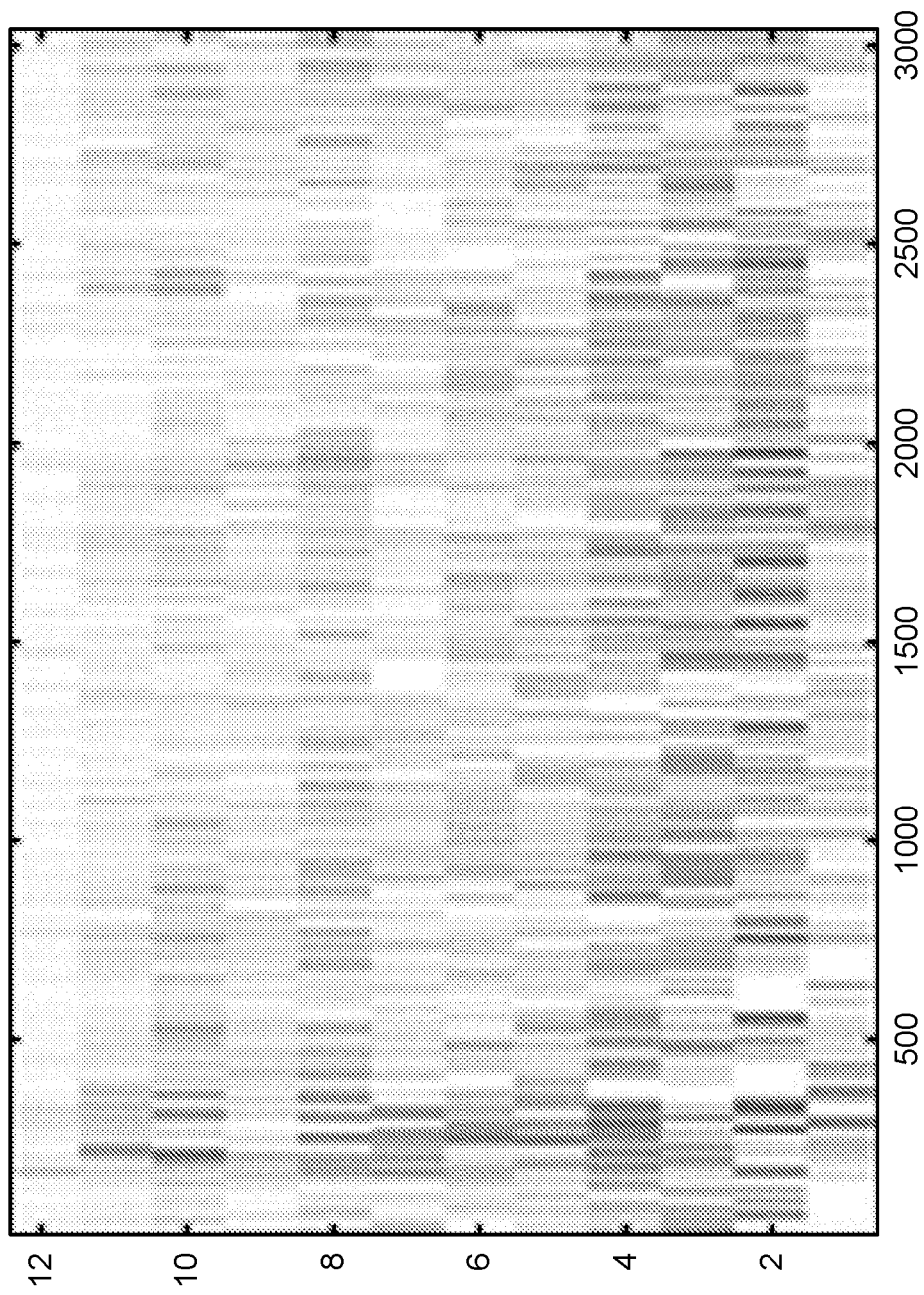

FIGS. 8A-8B show examples of left and right band pass envelopes respectively for a speech signal presented at 60 dB SPL from −60° azimuth in a quiet sound environment. FIGS. 9A-9B show similar examples of left and right band pass envelopes for the same speech signal presented at 60 dB SPL from −60° azimuth in a sound environment with noise at 60 dB SPL presented from 60° azimuth. Applying a bilateral channel selection (M×(1-of-2)) with identical band passes results in masked envelopes as depicted in FIGS. 10A-10B where the spectro-temporal characteristics of the original left side signal are reconstructed.

Bilateral signal processing arrangements according to embodiments of the present invention result in the spectral shape of left and right side signals being the same, and especially the same harmonic structure will be stimulated on the left and right side. This may be especially beneficial for perception of musical signals. Although the description refers only to band pass amplitudes, it is readily understood that the invention is equally workable with band pass envelope amplitudes.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for hearing implants other than cochlear implants such as an auditory brainstem implant.

What is claimed is:

1. A method of signal processing in a bilateral hearing implant system having left side and right side hearing implants, the method comprising:
sensing left side and right side sound environments with left side and right side sensing microphones to develop corresponding left and right microphone signals;

preprocessing the left and right microphone signals to generate a plurality of band pass signals for each side, each band pass signal representing an associated band of audio frequencies; and processing the band pass signals in a time sequence of stimulation frames, wherein for each stimulation frame, the processing includes:
  i. synchronously selecting a set of stimulation channels for each side based on spectral content of the band pass signals, and
  ii. processing a limited subset of each side band pass signals corresponding to the selected stimulation channels to generate electrical stimulation signals for the left side and right side hearing implants.

2. The method according to claim 1, wherein the synchronously selecting uses a composite set of combined left and right band pass signals.

3. The method according to claim 2, wherein the synchronously selecting includes processing the composite set of combined left and right band pass signals using one or more masking models.

4. The method according to claim 1, wherein the synchronously selecting uses a master-slave arrangement wherein one side of the bilateral hearing implant system is selected to be a master side configured for selecting the stimulation channels, and wherein the other side of the bilateral hearing implant system is a slave side configured for using the selected stimulation channels from the master side.

5. The method according to claim 4, wherein the master side is the side on which the microphone signals are loudest.

6. The method according to claim 4, wherein the master side is the side on which a dominant sound object is located.

7. The method according to claim 1, wherein the synchronously selecting chooses a defined number of greatest amplitude band pass signals independently of side.

8. A computer program product implemented in a non-transitory, tangible computer readable storage medium for signal processing in a bilateral hearing implant system having left side and right side hearing implants, the product comprising:
  program code for sensing left side and right side sound environments with left side and right side sensing microphones to develop corresponding left and right microphone signals;
  program code for preprocessing the left and right microphone signals to generate a plurality of band pass signals for each side, each band pass signal representing an associated band of audio frequencies;
  program code for processing the band pass signals in a time sequence of stimulation frames, wherein for each stimulation frame, the processing includes:
  i. synchronously selecting a set of stimulation channels for each side based on spectral content of the band pass signals, and
  processing a limited subset of each side band pass signals corresponding to the selected stimulation channels to generate electrical stimulation signals for the left side and right side hearing implants.

9. The product according to claim 8, wherein the synchronously selecting uses a composite set of combined left and right band pass signals.

10. The product according to claim 9, wherein the synchronously selecting includes processing the composite set of combined left and right band pass signals using one or more masking models.

11. The product according to claim 8, wherein the synchronously selecting uses a master-slave arrangement wherein one side of the bilateral hearing implant system is selected to be a master side configured for selecting the stimulation channels, and wherein the other side of the bilateral hearing implant system is a slave side configured for using the selected stimulation channels from the master side.

12. The product according to claim 11, wherein the master side is the side on which the microphone signals are loudest.

13. The product according to claim 11, wherein the master side is the side on which a dominant sound object is located.

14. The product according to claim 8, wherein the synchronously selecting chooses a defined number of greatest amplitude band pass signals independently of side.

15. A signal processing system for signal processing in a bilateral hearing implant system having left side and right side hearing implants, the arrangement comprising:
  left side and right side sensing microphones configured for sensing left side and right side sound environments to develop corresponding left and right microphone signals;
  left side and right side filter bank pre-processors configured for preprocessing the left and right microphone signals to generate a plurality of band pass signals for each side, each band pass signal representing an associated band of audio frequencies;
  a bilateral signal processing arrangement configured for processing the band pass signals in a time sequence of stimulation frames, wherein the signal processing module includes:
  i. a bilateral channel selection module configured for synchronously selecting for each stimulation frame a set of stimulation channels for each side based on spectral content of the band pass signals; and
  ii. left side and right side signal processing submodules configured for processing for each stimulation frame a limited subset of each side band pass signals corresponding to the selected stimulation channels to generate electrical stimulation signals for the left side and right side hearing implants for perception as sound by an implanted patient.

16. The system according to claim 15, wherein the bilateral channel selection module is configured for synchronously selecting using a composite set of combined left and right band pass signals.

17. The system according to claim 16, wherein the bilateral channel selection module is configured for synchronously selecting including processing the composite set of combined left and right band pass signals using one or more masking models.

18. The system according to claim 15, wherein the bilateral channel selection module is configured for synchronously selecting using a master-slave arrangement wherein one side of the bilateral hearing implant system is selected to be a master side configured for selecting the stimulation channels, and wherein the other side of the bilateral hearing implant system is a slave side configured for using the selected stimulation channels from the master side.

19. The system according to claim 18, wherein the master side is the side on which the microphone signals are loudest.

20. The system according to claim 18, wherein the master side is the side on which a dominant sound object is located.

21. The system according to claim 15, wherein the bilateral channel selection module is configured for synchronously selecting by choosing a defined number of greatest amplitude band pass signals independently of side.

* * * * *